United States Patent [19]

Molinaro et al.

[11] 4,130,634
[45] Dec. 19, 1978

[54] METHOD FOR DETECTING AND QUANTIFYING ANTIGENS

[75] Inventors: Giuseppe A. Molinaro; Sheldon Dray, both of Chicago, Ill.

[73] Assignee: University of Illinois Foundation, Urbana, Ill.

[21] Appl. No.: 713,348

[22] Filed: Aug. 11, 1976

Related U.S. Application Data

[63] Continuation-in-part of Ser. No. 451,685, Mar. 15, 1974, abandoned.

[51] Int. Cl.$^2$ .................. G01N 13/00; G01N 21/06; G01N 31/00; G01N 33/00
[52] U.S. Cl. .................. 424/8; 23/230 B; 424/11; 424/12; 424/13; 422/57
[58] Field of Search .................. 424/8, 11, 12, 13; 23/230 B, 253 TP

[56] References Cited

PUBLICATIONS

Molinaro, Fed. Proc., vol. 32, Mar. 1973, Ab. No. 4169.
Baker, Applied Microbiol., vol. 17, 1969, pp. 422–426.
Rangel, Immunology, vol. 14, 1968, pp. 197–211.

*Primary Examiner*—Albert T. Meyers
*Assistant Examiner*—A. P. Fagelson
*Attorney, Agent, or Firm*—Merriam, Marshall & Bicknell

[57] ABSTRACT

Method for detecting and quantifying an antigen by contacting with erythrocytes coated with antibody specific to the antigen and reactive therewith, followed by treatment with developer comprising antibody reactive with the antigen and with complement. Lysis of the erythrocytes serves to detect the presence of the antigen or of a cell secreting the antigen.

4 Claims, No Drawings

METHOD FOR DETECTING AND QUANTIFYING ANTIGENS

This application is a continuation-in-part of our co-pending application Ser. No. 451,685, filed March 15, 1974, now abandoned.

This invention relates to a method for detecting and/or quantifying an antigen in solution, and for enumerating cells which secrete the antigen, by the use of erythrocytes which have been coupled with an antibody specific to the antigen and which retains its reactivity therewith.

It is known that a variety of antigens can be coupled to erythrocytes (red blood cells) and that the antigen-coated erythrocytes can be used for the detection of the corresponding antibody (A. B. Stavitsky, J. Immunol., 74:360, 1954). In contact with the antibody, the antigen-coated erythrocytes exhibit certain immunological phemomena, such as agglutination and hemolysis, which serve to indicate the presence of the antibody in a substance under test. Although the methods of the prior art permit the detection of antibodies, no similar method has been available for quantifying antigens in solution or for counting the cells in a sample which secrete a particular antigen.

The invention provides a method which permits the detection and quantification of an antigen in solution, and the enumeration of cells secreting an antigen, by the use of erythrocytes which have been coated or coupled with an antibody specific to the antigen of interest. When the coated erythrocytes are brought into contact with an antigen-containing solution, or with antigen-secreting cells, in accordance with the procedures to be described, lysis of the erythrocytes occurs if the antigen corresponding to the antibody with which the erythrocytes have been coated is present in the system. The existence and extent of lysis of the erythrocytes provide a basis for detecting the presence of the antigen, for determining the concentration thereof, and for enumerating the cells in the system which secrete the antigen.

The method of the invention employs as a reagent erythrocytes which have been "coated", or "covered" with, or which have "coupled" thereto, a particular antibody. It should be understood that, regardless of the method used to attach the antibody to the erythrocyte, the antibody must retain its reactivity with its corresponding antigen. In this connection, the antibody-coated erythrocytes of the invention (herein referred to as "Ab-E") must be distinguished from materials known in the prior art which might be considered to be "antibody-coated erythrocytes", in which the antibodies used for coating are those specific to the erythrocyte and which bind thereto directly because the binding sites of the antibody molecules have specificity for the erythrocyte. After reaction with the erythrocyte, however, the antibody in such products is no longer reactive because the binding sites thereof are blocked. Such "antibody-coated erythrocytes" in which the antibody no longer has reactivity cannot be used in the present invention and must be distinguished from the antibody-coated erythrocytes contemplated herein.

The antibody-coated erythrocytes contemplated for use in the invention can be prepared by any known method useful for attaching proteins to erythrocytes, such as that described by Vyas et al. (J.Immunol. 100:274, 1968). Suitable antibody-coated erythrocytes can be prepared by the use of chemical coupling agents which form covalent bonds between the antibody and the erythrocytes, such as bisdiazotized benzidine; 1,3-difluoro-4,6-dinitrobenzene, tolylene-2-diisocyanate, and water soluble carbodiimide. Coupling agents which form non-covalent bonds between the erythrocytes and the antibody can also be used, such as tannic acid and chromium chloride.

Another method for preparing the antibody-coated erythrocytes used in the invention uses hybrid antibody which has been prepared to have one binding site specific to the erythrocyte (as an antigen) and the other binding site specific to the antigen under test. Erythrocytes can be coated with such hybrid antibody without the use of a chemical coupling agent. When erythrocytes are brought into contact with hybrid antibody of this type, the reaction between the erythrocyte and the binding site of the antibody specific thereto causes the antibody to be attached to the erythrocyte, leaving, however, the other binding site on the antibody available for reaction with its corresponding antigen.

In another method which does not require a chemical reagent for the attachment of antibody (Ab) to erythrocytes (E) the erythrocytes are modified in such a way that the membrane can fix antibody directly. For this purpose the erythrocytes are first coated with Protein A (a single polypeptide chain having a molecular weight of about 42,000; commercially available from Pharmacia Fine Chemicals, Inc., Piscataway, N.J.), washed and then mixed with purified Ab. Since Protein A has a natural ability to bind IgG antibody, the Protein A-coated erythrocytes will bind the antibody and will therefore become "supercoated" therewith. Since no chemical reagent is needed in the coupling of Ab to E, this method is preferred because the Ab molecules are not adversely affected, as may occur in treatment with chemical bonding reagents.

For preparation of antibody-coated erythrocytes to be used in the invention, the source of the eythrocytes is not critical, and erythrocytes from any animal source, such as man, sheep, rabbit, or mouse can be used. It is essential, however, that the antibodies used be those which are specific to the antigen for which the antibody-covered erythrocytes will be used as a probe. In order to improve the reactivity of the antibody-coated erythrocytes it is desirable to use in the preparation thereof an antibody fraction which has been purified so as to increase the concentration of the desired antibody therein. Suitable methods for such purification are known and will be apparent to those skilled in the art.

In one variant (spot lysis), the method of the invention involves bringing a material, known or believed to contain in solution a particular antigen, into contact with erythrocytes coated with antibody reactive with the particular antigen, as previously described. If the antigen is present in the system, it will bind to the antibody-coated erythrocytes and spot lysis of the erythrocytes will occur on treatment first with an antibody specific for the bound antigen (developer) and then with complement.

In another variant (radial lysis), the method of the invention can be used for quantification of antigen by single radial immune hemolysis. In this procedure, an antigen of unknown concentration is allowed to diffuse from a well into a medium such as agar gel which contains antibody-coated erythrocytes. After a standard period of time, a developer, i.e., an antiserum containing antibody reactive with the bound antigen, and complement are added, causing localized hemolysis to develop around the well. At low antigen concentration, the area of the hemolytic circle is proportional to the concentration of the antigen, which can be determined (to a sensitivity on the order of 0.1 μg/ml) from standards constructed using known concentrations of antigen.

In a third variant (localized hemolysis) of the method of the invention, antigen-mediated lysis of antibody-coated erythrocytes is used to detect and enumerate antigen-secreting cells by a plaque-forming cell (PFC) assay. In this procedure, antibody-coated erythrocytes serve as an indicator for the presence of cells secreting the corresponding antigen. In general, the procedure consists of mixing a known number of cells, including those secreting a particular antigen, with erythrocytes coated with antibody specific to the antigen and with a suitable gel-forming material, such as agar gel, and plating the composition on a suitable surface such as a petri dish. After a period of incubation, the surface is treated with developer and complement. The presence of a cell secreting the particular antigen is indicated by the appearance of a hemolytic circle on the surface surrounding the cell. Enumeration of the hemolytic circles permits calculation of the concentration of particular cells in the original mixture. The PFC assay of the invention provides a general method for detecting antigen-secreting cells, regardless of the cell type. The method differs from the cytochemical and cytoimmunochemical methods heretofore known, by probing for secretion rather than intracellular presence of antigen, and is particularly suitable for enumerating lymphocytes which secrete immunoglobulins in samples of blood or body tissue.

The invention is illustrated by the examples set out below, in which the following materials and procedures were used.

Antisera

The antisera to mouse serum albumin (MSA), to human immunoglobulin (Ig), to mouse gammaglobulin (MGG), and to sheep erythrocytes (SE) were produced according to standard methods.

Antibodies

Antibodies to MSA and to human Ig were isolated according to the method of Axen and Ernback (*Eur. J. Biochem.*, 18, 351, 1971). Antibodies to sheep erythrocytes (SE) were isolated according to the method of Bratcher et al. (*J. Immunol.*, 112, 373, 1974). Hybrid antibodies were prepared from purified antibody to SE and to humn Ig according to the method of Nisonoff and Palmer (*Science*, 143, 376, 1964).

Cells

Human peripheral blood lymphocytes were isolated by the Ficoll-Hypaque method (Boyum, A., *Scand. J. clin. Lab. Invest. Suppl.*, 21, 97, 1968) and washed 4 times with Hanks' balanced salt solution (HBSS).

Coating the Erythrocytes (a) With Cr Cl$_3$

One volume of washed and packed sheep erythrocytes and one volume of purified anti-Ig antibody (1 mg/ml in 0.15 M NaCl) were mixed. Then one volume of CrCl$_3$.6H$_2$O (1 mg/ml in 0.15 M NaCl) was added. The three components were mixed and allowed to react at 18° C. for 5 minutes. The coated erythrocytes (Ab-E) were washed three times with 0.15 M NaCl and resuspended to 10% v/v in 0.15 M NaCl.

(b) With hybrid antibody

Hybrid antibody preparations were used to coat SE through the binding site directed against SE. SE ($10^{10}$ cells) were incubated with 0.2–0.5 mg of hybrid antibody in a final volume of 2 ml of saline at 20° for 30 minutes and then washed with saline.

(c) With Protein A

Erythrocytes were first coated with Protein A by the CrCl$_3$ method as described above. The Protein A-coated E ($10^{10}$ cells) were then incubated with 100 μg. of purified Ab in a final volume of 2 ml saline at 20° C. for 30 minutes and finally washed with saline.

EXAMPLE 1

Spot lysis (Qualitative Assay for Antigens)

Two ml of 1% Ab-E and 0.8% agarose in 0.15 M NaCl were allowed to gel in a 60 mm plastic Petri dish. A droplet of a serial dilution of MSA was placed on the gel and allowed to absorb. Then 2 ml of a 1:100 dilution of developer (anti-MSA or anti-MGG antiserum) and 0.1 ml of guinea pig complement were added. The dishes were then incubated at 37° C. for 30 minutes.

The presence of mouse serum albumin (MSA) can be detected in about 30 minutes by using erythrocytes coated with antibody to MSA. These anti-MSA Ab-E lyse when treated sequentially with MSA (the specific antigen), anti-MSA antiserum (the specific antibody as developer) and complement (Table 1). The anti-MSA Ab-E do not lyse without developer. The lysis is specific, since the wrong developer, e.g., antiserum to mouse gamma globulin (MGG), does not give lysis. The lowest concentration of MSA, still mediating lysis of the Ab-E is 1 μg/ml.

TABLE 1

| | Lysis of Ab-E | | |
|---|---|---|---|
| Coating on E | Antigen | Developer (antiserum) | Lysis |
| Anti-MSA | MSA | — | — |
| | MSA | Anti-MSA | + |
| | MSA | Anti-MGG | — |
| None | MSA | Anti-MSA | — |

EXAMPLE 2

Radial Lysis (Quantitative Assay for Antigen)

Eleven milliliter of 1% Ab-E and 0.8% agarose in saline borate buffer were allowed to gel in a 10 cm Falcon Petri dish. Five μl of human IgG diluted in normal rabbit serum (NRS) absorbed with sheep erythrocytes were placed in punched wells. The dish was kept at 4° C. for 48 hr., then incubated with 4 ml of 1:100 dilution of rabbit anti-human Ig antiserum at 4° C. overnight and finally treated with 4 ml of 1:10 dilution of guinea pig complement at 37° C. for 2 hr.

Localized hemolysis developed around the wells. The area of the hemolytic circles, after 48 hr., is linearly proportional to the concentration of the antigen (Table 2). This radial immunohemolysis method has great sensitivity (on the order of 0.1 μg/ml).

TABLE 2

| Radial Lysis | |
|---|---|
| Relationship between Ab concentration and hemolytic area | |
| Human Ig μg/ml | Hemolytic area |
| 0.1 | 0.09 |

TABLE 2-continued

Radial Lysis
Relationship between Ab concentration and hemolytic area

| Human Ig μg/ml | Hemolytic area |
|---|---|
| 0.2 | 0.16 |
| 0.4 | 0.33 |
| 0.8 | 0.72 |
| 1.6 | 1.21 |

The coefficients of variability for intraplate and for interplate replicate assays were less than 10.

EXAMPLE 3

Localized Lysis (Reverse PFC Assay).

One-tenth milliliter of a 10% suspension of just washed anti-human Ig Ab-E and 0.1 ml of suspension of lymphocytes isolated from normal human blood at various cell concentrations were pipetted into a 10 × 75 mm glass culture tube containing 0.8 ml of 0.8% agarose (Sea Plaque, Marine Colloids, Inc., Rockland, Maine) in HBSS, pH 7.3, at 45° C. The contents of the tube were mixed and then plated on a 60 mm Falcon plastic Petri dish precoated with 4 ml of 0.8% agarose (Seakem, Marine Colloids, Inc.) in HBSS. After gelification of the top layer, the dishes were incubated first at 37° C. for 1 hr. in a humidified atmosphere containing 5% $CO_2$ and again with 1 ml of serial dilutions of developer (anti-human Ig antiserum) at 37° C. for 1 hr. After decanting the developer, the dishes were again incubated either immediately or on the following day with 1.0 ml of a 1:10 dilution of reconstituted guinea pig complement (Grand Island Biological Co., Grand Island, N.Y.) in HBSS at 37° C. for 1 hr. and finally stored at 4° C. until the plaques were counted.

The Ig-secreting lymphocytes secreted Ig molecules that reacted with the nearby anti-Ig antibody bound to the erythrocytes. These "Ig sensitized" indicator cells, when incubated sequentially with developer and complement, lysed to form hemolytic plaques. Lymphocytes, not treated with developer, did not form plaques; neither did lymphocytes not incubated with complement. (Table 3). To titrate the developer, replicate dishes were developed with dilutions of the developer. Lower dilutions (1:10 to 1:200) developed the maximal number of PFC. Higher dilutions (1:400 to 1:3200) developed fewer and fewer plaques. A 1:100 dilution of the developer was chosen as the optimal dilution.

TABLE 3

Specificity of the hemolytic plaque formed by human lymphocytes with anti-Ig Ab-E*

| Indicator Cells | Developer | Complement | PFC per $10^6$ cells |
|---|---|---|---|
| Anti-human Ig | + | + | 11,340 |
|  | + | − | 20 |
|  | − | + | 40 |
| Hybrid Ab (Anti SE/anti Ig) | + | + | 9,050 |
| Anti-Rabbit Ig | + | + | 20 |
| Uncoated E | + | + | 10 |

*The lymphocytes were plated with the tabulated indicator cells.

The foregoing detailed description has been given for clearness of understanding only, and no unnecessary limitations should be understood therefrom, as modifications will be obvious to those skilled in the art.

What is claimed is:

1. A method for detecting the presence of a particular antigen in a composition which method comprises contacting said composition with erythrocytes having coupled thereto antibodies specific to said antigen, adding a developer comprising antibody reactive with said antigen, adding complement, and noting lysis of said erythrocytes as a positive indication of the presence of said antigen.

2. The method of measuring the concentration of an antigen in solution which method comprises placing a standard volume of said solution in a well surrounded by a medium containing erythrocytes coated with antibodies reactive with the antigen under test, said medium permitting diffusion therethrough of said antigen solution, permitting said solution to diffuse through said medium for a standard time period, adding a developer comprising antibody reactive with said antigen, and adding complement, whereby a hemolytic area surrounding said well is produced, and measuring said area as a measure of the concentration of said antigen in said sample.

3. The method of claim 2 wherein said medium is agar gel.

4. A method for enumerating the cells in a cell population which secrete a particular antigen, which method comprises preparing a mixture comprising said cell population, a gel forming ingredient, and erythrocytes coated with antibody specific to said antigen;
    spreading said mixture on a surface and allowing a gel to form;
    treating said gel sequentially with a developer comprising antibody reactive with said antigen and with complement; and
    counting hemolytic areas in said gel as a measure of the number of cells which secrete said antigen.

* * * * *